United States Patent [19]

Datta

[11] Patent Number: 5,143,833
[45] Date of Patent: Sep. 1, 1992

[54] PROCESS FOR THE PRODUCTION OF SUCCINIC ACID BY ANAEROBIC FERMENTATION

[76] Inventor: Rathin Datta, 442 W. Melrose Ave., #3, Chicago, Ill. 60657

[21] Appl. No.: 301,788

[22] Filed: Jan. 25, 1989

Related U.S. Application Data

[63] Continuation-in-part of Ser. No. 873,031, Jun. 11, 1986, abandoned.

[51] Int. Cl.$^5$ .......................... C12P 7/46; C12P 1/04; C12N 1/20; C07C 51/42
[52] U.S. Cl. ................... 435/145; 435/252.1; 435/170; 435/822; 562/593; 562/590
[58] Field of Search ............ 435/144, 145, 822, 252.1, 435/170; 562/593, 590

[56] References Cited

U.S. PATENT DOCUMENTS 4,110,175  8/1978  Algren et al. .................... 426/34

FOREIGN PATENT DOCUMENTS 0249773  12/1987  European Pat. Off. ............ 435/145

OTHER PUBLICATIONS

The Merck Index, 1983, 10th ed. p. 234.
Gerhadt et al., Manuel of Methods for General Bacteriology, ASM, 1981, pp. 67–69.
Boyer, R, Modern Experimental Biochemistry, 1985, pp. 80–82.
Bergey's Manual of Systematic Bacteriology, Krieg et al. ed, 1984, pp. 604–605.
Hopgood et al., Aust. J. Biol. Sci., vol. 20, pp. 165–192 (1967).
Caldwell et al., J. Bacteriol., vol. 98, pp. 668–676 (1969).
Caspari et al., Arch Microbiol., vol. 135, pp. 16–24 (1983).
Davis et al., Int. J. Syst. Bacteriol., vol. 26, pp. 498–504 (1976).

*Primary Examiner*—Irene Marx
*Attorney, Agent, or Firm*—Quarles & Brady

[57] ABSTRACT

A method of producing succinic acid comprises growing a succinate producing microorganism in medium containing sodium ions an assimilable carbohydrate, other required nutrients and dissolved carbon dioxide at pH of about 5.8 to about 6.4. The succinic acid can be isolated from the fermentation broth if it is present in high enough concentrations by maintaining the pH at about 5.8 to about 6.4 and adding calcium hydroxide so that calcium succinate precipitates.

3 Claims, No Drawings

PROCESS FOR THE PRODUCTION OF SUCCINIC ACID BY ANAEROBIC FERMENTATION

RELATED CASE

This application is a continuation-in-part of my earlier application U.S. Ser. No. 873,031, filed Jun. 11, 1986, now abandoned.

FIELD OF THE INVENTION

This invention relates to an improved fermentation method for the production of succinic acid and a simple method of purifying the succinic acid.

BACKGROUND OF THE INVENTION

Succinic acid and its derivatives are widely used as specialty chemicals for applications in foods, pharmaceuticals, and cosmetics. Furthermore, succinic acid is a valuable 4-carbon intermediate useful for the production of 1,4-butanediol, tetrahydrofuran, and gammabutyrolactone.

Although the succinate ion is a common intermediate in the metabolic pathway of many organisms, there are no examples of any fermentation that produces succinate in large amounts or with high yields. For example, succinate is a key intermediate for anaerobic fermentations by propionate-producing bacteria, but it is only produced in low yields and in low concentrations.

Succinate is also produced by anaerobic rumen bacteria These bacteria include *Bacteroides ruminicola* (hereafter written *B. ruminicola*) whose growth and metabolism is described by Howlett, et al., *Applied Environ. Microbiol.*, 32, 274–283 (1976) and *Bacteroides amylophilus* (hereafter written *B. amylophilus*) whose culture and growth are described by Caldwell, et al., *J. Bacteriol.*, 98, 668–676 (1969) and by Hamlin, et al., *J. Bacteriol.*, 72, 548–554 (1956).

Although the rumen bacteria give higher yields of succinate than do the propionate-producing bacteria, the reported fermentations were run in very dilute solutions and gave a variety of products in generally low yields. Moreover, the rumen organisms tend to lyse after a comparatively short fermentation time, thereby, leading to unstable fermentations.

In 1961, Anderson and Ordal isolated a facultative anaerobe, *Cytophaga succinicans,* which produced succinate, acetate, and formate from dextrose with fixation of carbon dioxide, *J. Bact.,* 81, 139 (1961). However, this organism produced succinate in such low concentrations that it would not be economically feasible to recover succinic acid from the fermentation medium. Similar results were observed with the *Bacteroides fragilis* obtained from the gastrointestinal tract, Caspari, et al., *Arch Microbiol.,* 135, 16–24 (1983).

In order for a process for the preparation of succinic acid to be commercially attractive it should produce succinic acid in high yields and at high concentrations. In addition, there must be a simple method for purification of the succinic acid.

We have now discovered a method for the anaerobic fermentation of carbohydrates to succinate in high yields and with high productivity. Furthermore, the succinate is produced in sufficiently high concentration in the fermentation medium to permit economical recovery of succinic acid by simple purification method.

SUMMARY OF THE INVENTION

In accordance with this invention, there is provided an improved fermentation process for the production of succinic acid or succinate in high yields (i.e., over 50%) by the fermentation of carbohydrates with a succinate-producing bacterium The improved process comprises conducting the fermentation in an aqueous fermentation medium containing carbohydrates assimilable by the bacterium, sodium ions, nutrients required for growth of the bacterium, and dissolved carbon dioxide, wherein the initial carbohydrate concentration on the medium is between about 20 g/l and about 100 g/l and the pH of the medium is maintained between about 5.8 and 6.4 during the fermentation.

When the initial carbohydrate concentration is at least about 30 g/l, and calcium hydroxide or calcium carbonate are used to maintain the pH, the succinate which is formed in high yield (e.g. 50% or more) is converted to sparingly-soluble calcium succinate which precipitates from the reaction mixture, thereby, providing a simple method for the recovery and purification of the product.

DETAILED DESCRIPTION OF THE INVENTION

The fermentation process of this invention involves the fermentation of carbohydrates by a succinate-producing bacterium to form succinic acid and lesser amounts of other materials. In general, any strain of bacterium which forms primarily succinate can be employed. A useful strain for the practice of this invention is the strain of *Anaerobiospirillum succiniciproducens* (hereafter written *A. succiniciproducens*) which was originally deposited in the American Type Culture Collection, Rockville, Md., as ATCC 29305. It has been redeposited under the provisions of the Budapest Treaty as ATCC 53488, and is freely available.

The process of this invention was also followed using strains of the rumen bacteria, *B, amylophilus* and *B. ruminicola*. Although the yields of succinate obtained with these microorganisms were lower than those obtained using *A. succiniciproducens,* it is evident that the process can be used with a number of succinate-producing bacteria.

The carbohydrate used in the practice of this invention can be any carbohydrate that is fermented by the strain of bacterium used. For *A. succiniciproducens,* these carbohydrate sources include dextrose, sucrose, fructose, lactose, soluble starches, and corn syrups. The fermentation is conducted in an aqueous medium containing sodium ions and dissolved carbon dioxide. Nutrients and other growth factors needed for growth and reproduction of the microorganism employed are also added to the medium.

The concentration of carbohydrate in the medium is be about 20 g/l and about 100 g/l preferably between about 40 g/l and about 80 g/l. Carbohydrate concentrations above about 100 g/l give solutions with such high osmotic pressures that the organisms do not grow. Although the organisms will grow in solutions containing less than 20 g carbohydrate per liter, the concentration of product is so low that its recovery is not practical.

Carbon dioxide can be supplied to the fermentation medium in various ways. The medium can be sparged with $CO_2$ gas. The fermentation can be run in a pressurized reactor which contains carbon dioxide at superatmospheric pressure. The $CO_2$ can be mixed with other gases as long as the gases employed do not interfere with the growth and metabolism of the organism employed. Carbon dioxide can also be supplied to the fermentation medium by the addition of carbonates or bicarbonates which generate this gas under the conditions of the fermentation. The medium should contain dissolved $CO_2$ in equilibrium with a minimum of about 0.1 atmosphere partial pressure of carbon dioxide. In the preferred embodiment, the medium is saturated with carbon dioxide and the atmosphere contains about 0.3 atmosphere partial pressure of carbon dioxide or higher.

In order to obtain good production of succinate, the pH of the medium is maintained in the range of from about 5.8 to about 6.4. At higher pH values, the main product is lactate rather than succinate, while at lower pH values, the fermentation is inhibited. The pH is conveniently maintained by the addition of alkaline carbonates, alkaline earth hydroxides, or mixtures thereof.

The fermentation process of this invention is carried out at a temperature between about 20° C. and about 49° C. Optimum growth of the *A. succiniciproducens* organism is about 39° C. Since this is a strict anaerobe, fermentations using the organism are carried out under anaerobic conditions in a medium which has been sterilized by heat or other means well known in the fermentation art.

The following examples further describe the embodiments of this invention. All parts are by weight and all percentages are by weight unless expressly stated to be otherwise.

Products of the fermentation were determined using high-performance liquid chromatography (HPLC). Components were analyzed chromatographically by elution with 0.006N $H_2SO_4$ from a cation-exchange resin in the hydrogen form. The eluted components were detected by means of a differential refractometer, plotted on a recorder and quantitated using an electronic integrator. The area under the curve, which represents the concentration of each component, is reported as a percentage of the total area. The general procedure is that given in "Analysis of Carbohydrate Mixtures by Liquid Chromatography", *Am. Soc. Brew. Chem. Proc.*, 1973, pp. 43–46. The separations were made on a 1-foot HPX-87 column in the hydrogen form, available from Bio-Rad Laboratories, Richmond, Calif. The carbohydrate was determined by a YSI dextrose analyzer (Yellow Springs Instrument Company, Yellow Springs, Ohio) using standard methods. It was reported as grams per liter of dextrose.

EXAMPLE 1

*A. succiniciproducens*, ATCC 53488 (ATCC 29305), was grown and maintained under strict anaerobic conditions. Anaerobic conditions were established by the use of a cysteine.HCl-$Na_2S.9H_2O$ reducing agent and an anaerobic glove box containing an atmosphere of 5% $H_2$, 5% $CO_2$, and 90% $N_2$.

Seed cultures of *A. succiniciproducens* were grown in medium of the following composition: dextrose—20 g/l polypeptone—10 g/l, yeast extract—5 g/l, $K_2HPO_4$—3 g/l, NaCl—1 g/l, $(NH_4)_2SO_4$—1 g/l, $MgCl_2.6H_2O$—0.2 g/l, $CaCl_2.2H_2O$—0.2 g/l. To 100 ml of heat-sterilized medium in a 125-ml Erlenmeyer flask in an anaerobic glove box was added 1.0 ml of 0.03M $Na_2CO_3$ followed by 0.15 ml of 0.18M $H_2SO_4$. A 0.5 ml solution of the following reducing agent was added: Cysteine.HCl—0.25 g/l, $Na_2S.9H_2O$—0.25 g/l. After 20 minutes, the reduced flasks were inoculated with frozen stock cultures (−70° C.) of *A. succiniciproducens*. The seed flasks were incubated at 39° C. overnight.

Seed culture (50 ml) from the seed flask was used to inoculate 1 liter of fermentation medium in a standard 1.4-liter New Brunswick Bioflo, Model C-30, fermenter. The fermentation medium had the following composition (g/l):

| | |
|---|---|
| Dextrose | 50 |
| Polypeptone | 10 |
| Yeast Extract | 5 |
| $K_2HPO_4$ | 1.0 |
| $NH_4Cl$ | 0.4 |
| $CaCl_2.2H_2O$ | 0.2 |
| $MgCl_2.6H_2O$ | 0.2 |
| $FeSO_4.7H_2O$ | 1 ppm (as Fe) |

Before inoculation, the medium was autoclaved for 20 minutes, 15 psi at 121° C. The reactor was cooled without agitation and a $CO_2$ sparge (100% $CO_2$) was utilized (10 ml/min) throughout cooling and temperature adjustment to 39 C. Ten milliliters of a sterilized 3M $Na_2CO_3$ solution was added followed by 1.5 ml of concentrated $H_2SO_4$ to supply sodium ions and adjust the pH of the reactor to 6.8.

A 5-ml aliquot of a reducing solution (cysteine.HCl-$Na_2S.9H_2O$) was added and the fermentor was allowed to agitate at 200 rpm for 20 minutes before inoculation.

The temperature was controlled at 39° C., the mixture was agitated at 200 rpm, and a 10 ml/min $CO_2$ sparge (100% $CO_2$) was employed throughout the fermentation. The pH of the fermentation was allowed to drop to 6.4 and was maintained at 6.4 by addition of a sterile solution of 2M $Na_2CO_3$. Fermentation was rapid with *A. succiniciproducens* establishing a high cell population within 16 hours. The cells were motile at the beginning (0–24 hours) and then became nonmotile towards the end. The fermentation lasted 38 hours at which time there was <0.5 g/l dextrose remaining in the reactor. A total of 215 ml of 2M $Na_2CO_3$ was added for pH control during the course of the fermentation. The fermentation results are shown in Table I.

TABLE I

| | Concentration (grams/liter) | Volume (liters) | Total (grams) |
|---|---|---|---|
| Dextrose (initial) | 47.5 | 1.0 | 47.5 |
| Dextrose (final) | 0.5 | 1.24 | 0.6 |
| Products (at 38 hours) | | | |
| Succinate | 33.2 | 1.24 | 41.2 |
| Acetate | 9.3 | 1.24 | 11.5 |
| Formate | 0.4 | 1.24 | 0.5 |
| Lactate | 0.0 | 1.24 | 0.0 |

$$\text{Succinate Yield} = \frac{41.2 \text{ g Succinate}}{46.9 \text{ g Dextrose Utilized}} \times 100 = 87.8\%$$

COMPARATIVE TEST 1

The procedure of Example 1 was followed except that a nitrogen gas sparge was substituted for the $CO_2$ sparge. The reactor was reduced with a 5-ml aliquot of reducing agent, cysteine.HCl-$Na_2S.9H_2O$, before inoculation.

A 10-ml aliquot of 3M $Na_2CO_3$ followed by 1.5 ml concentrated $H_2SO_4$ was added to the reactor. (Addition of carbonate was necessary to initiate growth.) The pH of the fermentation was controlled at 6.4 with the addition of 4N NaOH. The cells of *A. succiniciproducens* became swollen and the fermentation was sluggish. The fermentation was stopped after 40 hours and the products were analyzed. The results given Table II show that the fermentation run without dissolved carbon dioxide produces very little succinic acid and a number of by-products.

TABLE II

|  | Grams/Liters |
|---|---|
| Products |  |
| Lactate | 13.5 |
| Acetate | 0.8 |
| Formate | 1.5 |
| Succinate | 0.6 |
| Ethanol | 1.2 |
| Substrate |  |
| Dextrose (initial) | 40.0 |
| Dextrose (final) | 17.5 |
| Net Dextrose Utilized | 22.5 |

Succinate Yield = $\frac{0.6}{22.5} \times 100 = 2.6\%$

Lactate Yield = $\frac{13.5}{22.5} \times 100 = 60\%$

EXAMPLE 2

The general procedure of Example 1 was modified as follows. The iron salt was omitted from the medium and 0.5 g/l of NaCl was added to supply sodium ions. The $CO_2$ sparge (100% $CO_2$) was stopped after inoculation; so the only source of $CO_2$ in the fermentation was from the 3M $Na_2CO_3$ which was used for pH control. The pH was maintained at pH 6.4±0.1. This fermentation, without a $CO_2$ sparge, did not initiate as rapidly as the fermentation conducted with a $CO_2$ sparge. Analyses of products after a 40-hour fermentation are given in Table III.

TABLE III

|  | Concentration (grams/liter) | Volume (liters) | Total (grams) |
|---|---|---|---|
| Dextrose (initial) | 53.8 | 1.0 | 53.8 |
| Dextrose (final) | 15.6 | 1.1 | 17.2 |
| Net Dextrose Utilization |  |  | 36.6 |
| Products (at 40 hours) |  |  |  |
| Succinate | 30.5 | 1.1 | 33.6 |
| Acetate | 8.2 | 1.1 | 9.0 |
| Formate | 1.7 | 1.1 | 1.9 |
| Lactate | 0.5 | 1.1 | 0.55 |

Succinate Yield = $\frac{33.6}{36.6} \times 100 = 91.8\%$

EXAMPLE 3

Three fermentations were run using the general procedure of Example 2 except that the pHs of these fermentations were controlled at 5.9±0.1; 6.8±0.1; and 7.2±0.1, respectively. The results of these experiments are given in Table IV. When the fermentation was run at pH 5.5±0.1, the fermentation was very slow and a low concentration of succinate was produced.

These results together with the results of Example 2 indicate that the production of succinate proceeds best in a medium where the pH is rigidly maintained between about 5.8 and about 6.4.

TABLE IV

|  | pH 5.9 | pH 6.8[a] | pH 7.2[a] |
|---|---|---|---|
| Dextrose (initial) | 58.0 | 57.3 | 59.3 |
| Dextrose (final) | 1.9 | 1.6 | 1.8 |
| Fermentation Time (hrs) | 24 | 29 | 41 |
| Products |  |  |  |
| Succinate | 50.3 | 20.2 | 14.7 |

TABLE IV-continued

|  | pH 5.9 | pH 6.8[a] | pH 7.2[a] |
|---|---|---|---|
| Acetate | 13.6 | 5.4 | 4.3 |
| Formate | 1.3 | 2.1 | 1.7 |
| Lactate | 0 | 20.6 | 39.6 |
| Succinate Yield (%) | 89.7 | 36.3 | 25.6 |
| Lactate Yield (%) | 0 | 37.0 | 68.9 |

[a]Comparative test

EXAMPLE 4

The general procedure of Example 1 was followed using a medium containing 50 g/l of dextrose except that after the initial pH adjustment with $Na_2CO_3$ and $H_2SO_4$, the pH was maintained at 6.4 by the addition of a 25% slurry of $Ca(OH)_2$ in water, and the fermentation temperature was 37° C.

The fermentation proceeded more rapidly than did the fermentation of Example 1 where the pH was maintained by addition of $Na_2CO_3$ solution. At 21 hours from startup, there was a sudden solidification of reactor contents. The solid was separated and the contents of both the solid and solution were analyzed. About 99% of the dextrose had been consumed. The yield of products is given in Table V. These results show that the production of succinic acid occurs rapidly when the fermentation is run in the presence of calcium hydroxide and indicates that the succinic acid can be separated from the fermentation medium as the sparingly-soluble calcium salt. Since calcium succinate monohydrate is less soluble at higher temperatures, more product can be recovered from the fermentation broth by heating it to 80°–90° C. and recovering the resulting precipitate.

TABLE V

| Product Yield[a] | In Solution (grams) | In Solid (grams) | Total (grams) |
|---|---|---|---|
| Succinate | 18.6 | 21.0 | 39.6 |
| Acetate | 9.6 | 1.3 | 10.9 |
| Formate | 1.2 | 0.0 | 1.2 |

[a]Yield based on carbohydrate utilized:
Succinate-80%
Acetate-22%
Formate-2%

EXAMPLE 5

The general procedure of Example 1 was followed using as strain of rumen bacterium, *B. amylophilus* (available from the Deutsche Sammlung Von Microorganismen, Grisebachstr. 8, 34 Gottingen, Federal Republic of Germany, as DSM 1361), using the following medium in which the concentrations are given in grams per liter unless otherwise indicated:

| $K_2HPO_4$ | 0.9 |
|---|---|
| $KH_2PO_4$ | 0.9 |
| NaCl | 1.8 |
| $(NH_4)_2SO_4$ | 1.8 |
| $CaCl_2 \cdot 2H_2O$ | 0.18 |
| $MgSO_4 \cdot 7H_2O$ | 0.4 |
| $FeSO_4 \cdot 7H_2O$ | 2 ppm (as Fe) |
| Maltose·$H_2O$ | 50 |
| Resazurin | 1 ml |
| Cysteine·HCl·$Na_2S \cdot 9H_2O$ | 5 Ml |

The addition of maltose was necessary because *B. amylophilus* does not utilize glucose. The fermentation proceeded very rapidly and was completed after 21 hours. Cells of *B. amylophilus* began to lyse after 12 hours as indicated by a decline in optical density and cell mass in the fermentation. Analyses of the products given Table VI indicate that this strain of rumen bacterium produces succinic acid under the conditions of this invention.

TABLE VI

| Products (at 21 hours) | Grams/Liter |
|---|---|
| Succinate | 11.9 |
| Acetate | 2.9 |
| Formate | 3.2 |
| Dextrose (initial) | 40.5 |
| Dextrose (final) | 17.8 |
| Net Utilized | 22.7 |

Succinate Yield = $\frac{11.9}{22.7} \times 100 = 52.4\%$

EXAMPLE 6

The general procedure of Example 1 was followed except that the microorganism used was a strain of the rumen bacterium, B. ruminicola, available from the American Type Culture Collection, Rockville, Md., as ATCC 19188. The results given in Table VII show that this strain of rumen bacterium, like that of Example 4, also produces succinic acid by the process of this invention. Succinate yields obtained from these bacteria using the process of this invention are much higher than yields obtained from these bacteria by previously-reported processes. However, succinate yields from rumen bacteria are lower than those obtained with A. succiniciproducens.

TABLE VII

| Products (at 62 hours) | Grams |
|---|---|
| Succinate | 18.9 |
| Acetate | 5.4 |
| Formate | 1.2 |
| Lactate | 1.8 |

Succinate Yield = $\frac{18.9 \text{ g Succinate}}{31.7 \text{ g Dextrose Utilized}} \times 100 = 59.5\%$

EXAMPLE 7

A series of fermentations was run in 160-ml serum bottles using 25 ml of a fermentation medium similar to that in Example 1. The concentration of dextrose was 38.2 g/l and the fermentation medium also contained 30 g/l of $MgCO_3$. The pH of the medium was adjusted to 6.8 and maintained at 6.4. The headspace in the bottles was filled with carbon dioxide at various pressures. At the end of 44 hours, the pressure was measured in the vessels and the contents of the aqueous medium were analyzed. In each flask, the yield of lactate was about 5% and the yield of acetate was about 23%. The yields of succinate at various pressures are given in Table VIII. They demonstrate that the yield of succinate increases as the pressure of the carbon dioxide gas in equilibrium with the fermentation increases above atmospheric pressure.

TABLE VIII

| Final Pressure (atm.) | Succinate Yield (%)[a] |
|---|---|
| 1.0 | 87.6 |
| 1.4 | 88.4 |
| 2.2 | 92.2 |
| 2.7 | 95.2 |

[a]Calculated as in Example 1.

EXAMPLES 8–21

Fermentations were run showing the carefully controlled conditions of pH, $CO_2$ partial pressure, critical cation ($Na^+$) concentration, and critical substrate concentration lead to high yield, high rate fermentation and the simultaneous production of calcium succinate in the fermenter. Examples showing the effects of $CO_2$ partial pressure, pH, sodium concentration, substrate concentration, and the source of calcium on calcium succinate precipitation are presented.

The fermentation procedures and methods were the same as for Example 2 unless otherwise indicated. The seed culture medium was the same as in Example 1.

All gas flow rates were 10 ml/minute. The 10% $CO_2$ mixture contained a balance of $N_2$. The 30% $CO_2$ gas mixture was prepared by blending $CO_2$ and $N_2$ with a dual flowmeter/mixer. After sterilization the media was gassed with the indicated mixture. After inoculation the gas flow was directly into the headspace of the fermentor. The reagents used for initial pH adjustment were as follows:

| NaOH | 12 ml 3M NaOH + 1 ml $H_2SO_4$ |
|---|---|
| $Na_2CO_3$ | 10 ml 3M $Na_2CO_3$ + 1 ml $H_2SO_4$ |
| $Ca(OH)_2$ | 1 ml $H_2SO_4$ + 25% $Ca(OH)_2$ |

The concentrations of the reagents used for fermentation pH control were as follows:

| NaOH | 3M in water |
|---|---|
| $Na_2CO_3$ | 3M in water |
| $Ca(OH)_2$ | 25 wt % in water |

Glucose and acid concentrations determined by the previously described analytical methods are given as g/l based on initial volume. Carbonate analysis in the precipitated solids was determined by $CO_2$ evolution upon HCl addition plotted against a standard of $CaCO_3$. Solids were vacuum filtered through a Whatman #1 filter paper and dried at 60° C.

Table IX shows the effect of $CO_2$ partial pressure on the succinate productivity and yield. In all conditions, 30% $CO_2$ in the gas phase produced better results than 10% $CO_2$ in the gas phase. The use of 30% $CO_2$ and $Na_2CO_3$ for neutralization supplied the fermentation with the required $CO_2$ for typical desired succinate yields. However, even under these conditions the succinate productivity was reduced compared to 100% $CO_2$ gas phase. Comparison of Example 4 with Example 11 shows that with 100% $CO_2$ (partial pressure 1 atmosphere) the fermentation is completed in 21 hours (Example 4) as compared to only partial completion even at 42 hours at 30% $CO_2$ (Example 11).

Table X shows the effect of initial sodium concentration on the fermentation. Both 3.5 g NaCl and 10 ml 3M $Na_2CO_3$ contain 1.4 g of sodium. The fermentation without Na ions produced no growth or substrate consumption. These fermentations show that sodium ions are initially required. Thus, the fermentation proceeds and produces precipitated calcium succinate only under conditions when an initial concentration of sodium ions is present.

Table XI shows that undesired $CaCO_3$ formation is excessive and succinate concentrations are low when the fermentation is controlled at undesirable pHs of 6.5 and above. It should be noted that the pH was very difficult to control because of runaway calcium carbonate formation. The solids composition is also shown and the solids are primarily calcium carbonate. Comparison between Example 4 and Examples 16 and 17 shows that if the pH is not maintained at the desired range, the solids precipitate does not contain a substantial portion of succinate. Thus, a process for succinate recovery from the broth as calcium succinate is not feasible if the pH is not controlled at the optimum range of 5.8–6.4.

Table XII shows that the calcium ions cannot be added initially as $CaCl_2$. Addition of $CaCl_2$ to the fermentation at the level of 75 g/l completely inhibited the fermentation.

Table XIII shows a threshold of initial glucose concentration is necessary for calcium succinate precipitation. It also shows a typical composition of the solids recovered (in contrast with the pH 6.8 solids; see Example 16 and 17). The results show that below a threshold of initial glucose concentration simultaneous fermentation with precipitation of calcium succinate cannot occur. Note that the concentration of calcium succinate produced exceeds the saturation concentration at the temperature of the fermentation.

The results show that to produce a precipitated calcium succinate product, simultaneous control of initial substrate concentration, pH, addition of required cation (e.g. Na), and control of $CO_2$ partial pressure is needed.

TABLE IX

Results of Succinate Fermentation Using Various Partial Pressures of Carbon Dioxide in Gas Phase

| EXAMPLE | 8 | 9 | 10 | 11 | 12 | 13 |
|---|---|---|---|---|---|---|
| Carbon Dioxide Partial Pressure, (ATM) | 0.10 | 0.10 | 0.10 | 0.30 | 0.30 | 0.30 |
| Reagent for Initial pH Adjustment | $Na_2CO_3$ | NaOH | NaOH | $Na_2CO_3$ | NaOH | NaOH |
| Reagant for Fermentation pH Control | $Ca(OH)_2$ | NaOH | $Na_2CO_3$ | $Ca(OH)_2$ | NaOH | $Na_2CO_3$ |
| Fermentation Time, HRS. | 42.75 | 42.75 | 42.75 | 42.75 | 42.75 | 31.5 |
| SUBSTRATE, g/l | | | | | | |
| Dextrose, Initial | 48.6 | 49.2 | 47.3 | 45.2 | 45.2 | 47.5 |
| Dextrose, Final | 33.1 | 33.3 | 4.8 | 10.2 | 15.8 | 0.2 |
| Dextrose, Consumed | 15.3 | 15.9 | 42.5 | 35.0 | 29.4 | 47.3 |
| PRODUCTS, g/l | | | | | | |
| Succinate | 12.1 | 11.7 | 37.6 | 26.8 | 23.7 | 43.5 |
| Acetate | 4.7 | 4.5 | 9.9 | 9.4 | 6.9 | 11.4 |
| Formate | 1.3 | 1.1 | 0.9 | 3.9 | 2.4 | 1.0 |
| Lactate | 0.0 | 0.0 | 0.0 | 0.0 | 0.0 | 0.0 |
| PRODUCT YIELDS, WT % | | | | | | |
| Succinate | 78.1 | 73.6 | 88.4 | 76.6 | 80.6 | 91.5 |
| Acetate | 30.3 | 28.3 | 23.3 | 35.1 | 23.5 | 24.1 |
| Formate | 8.4 | 6.9 | 2.1 | 11.1 | 8.2 | 2.1 |
| Lactate | 0.0 | 0.0 | 0.0 | 0.0 | 0.0 | 0.0 |

[1]pH controlled at 6.2.

TABLE X

Results of Succinate Fermentation Showing the Effect of Initial Sodium Ion Concentration

| EXAMPLE | 14[a] | 15 |
|---|---|---|
| Sodium Chloride Conc., g/l | 0.0 | 3.5 |
| SUBSTRATE, g/l | | |
| Dextrose, Initial | 47.3 | 45.4 |
| Dextrose, Final | 47.3 | 0.7 |
| Dextrose, Consumed | 0.0 | 44.7 |
| PRODUCTS, g/l | | |
| Succinate | 0.0 | 40.7 |
| Acetate | 0.0 | 45.4 |
| Formate | 0.0 | 0.6 |
| Lactate | 0.0 | 0.0 |
| PRODUCT YIELDS, WT % | | |
| Succinate | 0.0 | 91.0 |
| Acetate | 0.0 | 23.7 |
| Formate | 0.0 | 1.3 |
| Lactate | 0.0 | 0.0 |
| FERMENTATION CONDITIONS | | | pH = 6.2; $CO_2$ = 100% (1 atmosphere)
Reagent for initial pH adjustment = $Ca(OH)_2$
Reagent for fermentation pH control = $Ca(OH)_2$

[a]Comparative test

TABLE XI

Succinate Fermentation at pH 6.8 Using Different Initial Dextrose Concentrations

| EXAMPLE | 16[a] | 17[a] |
|---|---|---|
| SUBSTRATE, g/l | | |
| Dextrose, Initial | 28.3 | 48.6 |
| Dextrose, Final | 0.2 | 24.1 |
| Dextrose, Consumed | 28.1 | 24.5 |
| PRODUCTS, g/l | | |
| Succinate | 23.8 | 17.2 |
| Acetate | 6.9 | 4.6 |
| Formate | 1.1 | 1.1 |
| Lactate | | |
| PRODUCT YIELDS, WT % | | |
| Succinate | 84.7 | 70.2 |
| Acetate | 24.6 | 18.8 |
| Formate | 3.9 | 4.5 |
| Lactate | | |
| SOLID PRODUCT | | |
| Total Solids, g | 46.1 | 110.0 |
| Succinate, WT % | 2.6 | 3.3 |

TABLE XI-continued

Succinate Fermentation at pH 6.8 Using
Different Initial Dextrose Concentrations

| EXAMPLE | 16[a] | 17[a] |
|---|---|---|
| Carbonate, WT % | 47.8 | 50.1 |
| FERMENTATION CONDITIONS | | |
| pH = 6.8; $CO_2$ = 100% (1 atmosphere) | | |
| Reagent for initial pH adjustment = $Na_2CO_3$ | | |
| Reagent for fermentation pH control = $Ca(OH)_2$ | | |
| Time of Fermentations = 29 Hrs | | |

[a] Comparative test

TABLE XII

Results Showing the Effect of
Initial Calcium Chloride Addition

| EXAMPLE | 18[a] |
|---|---|
| SUBSTRATE, g/l | |
| Dextrose, Initial | 46.4 |
| Dextrose, Final | 46.4 |
| Dextrose, Consumed | 0.0 |
| PRODUCTS, g/l | |
| Succinate | 0.0 |
| Acetate | 0.0 |
| Formate | 0.0 |
| Lactate | 0.0 |
| PRODUCT YIELDS, WT % | |
| Succinate | 0.0 |
| Acetate | 0.0 |
| Formate | 0.0 |
| Lactate | 0.0 |
| FERMENTATION CONDITIONS | |
| 75 g of Calcium Chloride added initially. | |
| Time of fermentation = 14.0 Hrs | |
| pH = 6.2; $CO_2$ = 100% (1 atmosphere) | |
| Reagent for initial pH adjustment = $Na_2CO_3$ | |
| Reagent for fermentation pH control = NaOH | |

[a] Comparative test

TABLE XIII

Succinate Fermentations Using
Various Initial Glucose Concentrations

| EXAMPLE | 19 | 20[a] | 21[a] |
|---|---|---|---|
| SUBSTRATE, g/l | | | |
| Dextrose, Initial | 29.3 | 25.3 | 18.8 |
| Dextrose, Final | 0.2 | 0.1 | 0.1 |
| Dextrose, Consumed | 29.1 | 25.2 | 18.7 |
| Fermentation Time (Hrs) | 20.0 | 14.0 | 14.0 |
| PRODUCTS, g/l | | | |
| Succinate | 26.1 | 23.2 | 16.5 |
| Acetate | 7.6 | 6.8 | 5.1 |
| Formate | 0.9 | 0.8 | 0.9 |
| Lactate | 0.0 | 0.0 | 0.0 |
| PRODUCT YIELDS, WT % | | | |
| Succinate | 89.7 | 92.1 | 88.2 |
| Acetate | 26.1 | 27.0 | 27.7 |
| Formate | 3.1 | 3.2 | 4.8 |
| Lactate | 0.0 | 0.0 | 0.0 |
| SOLID PRODUCT | | | |
| Total Solid, g | 23.5 | 0.0 | 0.0 |
| Succinate, WT % | 44.0 | | |
| Carbonate, WT % | 2.7 | | |
| pH = 6.2; $CO_2$ = 100% | | | |
| Reagent for initial pH control = $Na_2CO_3$ | | | |
| Reagent for fermentation pH control = $Ca(OH)_2$ | | | |

[a] Comparative test

Thus, it is apparent that there has been provided, in accordance with the invention, an both improved fermentation process for the production of succinic acid and a simple, effective method for precipitating the succinic acid as calcium succinate. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

I claim:

1. A method of producing succinate which comprises growing an anaerobic succinate producing microorganism which has all the identifying characteristics of *Anaerobiospirillum succiniciproducens* ATCC No. 53488 in a medium containing least about 20 g/l of an assimilable carbohydrate, other required nutrients and sodium ions under anaerobic conditions in the presence of dissolved carbon dioxide in equilibrium with a partial pressure of at least 0.1 atmosphere of carbon dioxide which maintaining the pH within the range of 5.8 to 6.4 until a substantial portion of the carbohydrate has been consumed and the yield of succinate is at least 50% by weight of the carbohydrate consumed and then recovering the succinate.

2. A method of claim 1 in which the dissolved carbon dioxide is supplied by dissolving carbonate in the medium.

3. A method of claim 1 in which the dissolved carbon dioxide is supplied by sparging with a gaseous mixture containing carbon dioxide.

* * * * *